United States Patent [19]

Hodes

[11] 3,987,281

[45] Oct. 19, 1976

[54] METHOD OF RADIATION THERAPY TREATMENT PLANNING

[75] Inventor: Louis Hodes, Rockville, Md.

[73] Assignee: The United States of America as represented by the Department of Health, Education and Welfare, Washington, D.C.

[22] Filed: July 29, 1974

[21] Appl. No.: 492,928

[52] U.S. Cl. .................... 235/151.3; 178/DIG. 5; 235/151; 235/198; 250/505; 444/1
[51] Int. Cl.² .................. G06F 15/42; A61N 5/01
[58] Field of Search ............. 235/151, 151.1, 151.3, 235/198, 184; 444/1; 178/DIG. 5; 250/505–513

[56] References Cited
UNITED STATES PATENTS 3,783,251   1/1974   Pavkovich ..................... 235/151
3,871,579   3/1975   Inamura ........................ 235/151.3

OTHER PUBLICATIONS

Umegaki: "Development of Computer Systems for Radiotharaphy of Cancer" Japan, *Journal of Clinical Oncology*, vol. 1, No. 1 Jan. 1971, pp. 65–82.
Sterling and Perry: "Computation of Radiation Dosages" *Computers in Biomedical Research*, vol. 1, 1965, pp. 439–464.
Sterling et al.: "The Dynamic Display of Radiation Therapy Plans Using Computer Produced Films" *Radiology*, vol. 107, No. 3, p. 689.
Weinkam et al.: *A Versatile System for Three-Dimensional Radiation Dose Computation and Display*, Computer Programs in Biomedicine 2, 1972, pp. 178–191.
Bahr et al.: *The Method of Linear Programming Applied to Radiation Treatment Planning*, Radiology No. 91, Oct. 1968, pp. 686–693.

*Primary Examiner*—Felix D. Gruber
*Attorney, Agent, or Firm*—Holman & Stern

[57] ABSTRACT

A technique of radiation therapy treatment planning designed to allow the assignment of dosage limits directly to chosen points in the computer-displayed cross-section of the patient. These dosage limits are used as constraints in a linear programming attempt to solve for beam strengths, minimizing integral dosage. If a feasible plan exists, the optimized plan will be displayed for approval as an isodose pattern. If there is no feasible plan, the operator/therapist can designate some of the point dosage constraints as "relaxed." Linear programming will then optimize for minimum deviation at the relaxed points. This process can be iterated and new points selected until an acceptable plan is realized. In this manner the plan is optimized for uniformity as well as overall low dosage.

6 Claims, 6 Drawing Figures

METHOD OF RADIATION THERAPY TREATMENT PLANNING

BACKGROUND OF THE INVENTION

Field of the Invention

The present invention is related to radiation therapy treatment planning and, more particularly, to a unique and novel radiation treatment therapy planning technique which allows direct assignment of dosage limits and utilizes linear programming to optimize for uniformity in the selection of radiation beam strengths which satisfy the selected dosage limit constraints.

DESCRIPTION OF THE PRIOR ART

Radiotherapy is the use of ionizing radiation for the treatment of patients suffering from a cancerous disease. Frequently, the tumor to be eradicated is positioned either deep within the patient or lies dangerously close to vital organs or structures that would be damaged by the radiation. Accordingly, one of the major problems in radiotherapy is to supply sufficient radiation at the site of the tumor to destroy it without at the same time harming the healthy tissues nearby. The determination of the optimum arrangement of one or several radiation beams and the calculation of the resultant dosage pattern is frequently referred to in the art as radiation treatment planning.

The calculation of a radiation dosage distribution which would result from a given number, size, orientation and strength of externally applied radiation beams is generally a time-consuming and tedious task. Many man-hours of labor are required to produce a radiation distribution which then, in the judgment of the radiotherapist, may or may not be acceptable for use.

The advent of digital computers has given rise to a number of machine-implemented techniques for producing radiation dosage distributions which have generally been successful in reducing the time-consuming task of determining an acceptable radiation dosage distribution for a particular patient's requirements. One such technique involves the use of a small computer system, referred to as the "Programmed Console", for calculating and displaying the dosage pattern, referred to in the art as isodose distributions, derived from multiple external radiation beams. See, for example, the article by W. F. Holmes entitled "External Beam Treatment Planning with the Programmed Console" which appeared in *Radiology*, Volume 94, No. 2, pages 391 through 400, February, 1970 such disclosure being incorporated herein by reference thereto. The foregoing system comprises a small digital computer, an input/output unit utilizing a magnetic card reader and writer, a display oscilloscope, and a position transducer or plotter for digitizing patient contours and isodose charts.

Briefly, the above-mentioned Programmed Console is utilized in the following manner. The patient contour is digitized by the position transducer which consists of an extendable arm rotating on a pivot, inside of which are two variable resistors which produce voltages dependent on the extension and angle of the arm. A computer program constantly samples the arm position, storing a set of digital numbers representing the coordinates of points spaced along the contour lines. After the patient contour and other areas of interest are traced and entered into the computer, the number of radiation beams selected are also entered, along with their desired size, orientation, and beam strength. Control knobs are provided on the input device which allow the operator to vary the position, angle, and source-to-skin distance of each beam. Based on this information, another computer program calculates the radiation dosage distribution or isodose pattern which would result from the application of the chosen radiation beams on the patient's contour. The intermediate solution in the form of a graphical representation of the resultant isodose lines, is displayed on the oscilloscope, and if it proves to be satisfactory, a hard copy may be output by a plotter. If the intermediate solution is unsatisfactory (in the judgment of the operator/therapist), the number, size, orientation, location and/or beam strength of the externally applied beams may be varied until an acceptable output is achieved.

It should be appreciated that the above-described technique merely does by computer what was previously done by hand. In terms of saving man-hours of labor, it is therefore extremely advantageous. However, such a technique fails in many respects to achieve optimum radiation treatment planning. This is primarily due to the fact that the beam strength of each of the external radiation beams are preselected and the resultant dosage distribution within the contour is examined for acceptability. This, by and large, requires an educated guess on the part of the therapist as to the correct beam strength necessary from each of the plurality of differently oriented radiation beams to produce the desired dosage at the critical internal points while, as stated above, attempting to minimize the resultant dosages at certain other predefined vulnerable positions within the patient. Accordingly, the time-honored method of trial and error remains basically unaltered in such a technique, although the time necessary for each trial has indeed been improved by the use of a computer.

A skilled radiotherapist, after being provided with a diagram of the cross section of a patient, has a fairly good idea of which beam directions and sizes to utilize in order to apply the major dose to the tumor and avoid sensitive areas. Of course, after the isodose distribution pattern is produced, factors such as maintaining a sufficient dosage over the tumor, providing a low integral dose, producing no hot spots, and the like, enable the skilled therapist to recognize an acceptable radiation treatment plan. However, the intermediate task which is not intuitive, even to the skilled therapist, is to select, in a multibeam plan, how strong each radiation field should be to achieve the desired results. It is within this framework wherein much improvement of the prior art technique is needed.

Accordingly, it would be highly advantageous if a technique for radiation therapy treatment planning were provided in which the therapist could preassign desired dosages to preselected points within the contour of a patient and thereafter determine the number, orientation, and importantly, the strength, of the radiation beams required to produce the desired dosage distribution.

OBJECTS AND SUMMARY OF THE INVENTION

A primary object of the present invention is to provide a novel and unique method for radiation therapy treatment planning.

Another object of the present invention is to provide a novel radiation treatment planning technique in which radiation beam strength for a plurality of radiation beams may be automatically computed in conformance with a desired preselected dosage distribution.

A further object of the present invention is to provide a unique radiation treatment planning method in which the desired radiation dosage distribution may be preselected and thereafter the number, size, orientation and beam strength of a plurality of radiation beams automatically determined to produce the desired dosage distribution.

An additional object of the present invention is to provide a novel radiation treatment planning technique in which linear programming is utilized to optimize for radiation uniformity as well as overall low dosage.

An additional object of the present invention is to provide a radiation therapy treatment planning technique which eliminates many disadvantages of prior art techniques in greatly reducing the trial and error iterations necessary to produce an acceptable radiation treatment plan.

The foregoing and other objects are attained in accordance with one aspect of the present invention through the provision of a method of radiation therapy treatment planning which comprises the steps of electronically plotting a contour representative of the areas of interest of the patient to be treated, and then selecting a predetermined number, size and orientation of radiation beams desired to be utilized. The method further includes the step of selecting predetermined radiation dosage limits corresponding to the desired dosages at a plurality of selected points within the contour. Thereafter, the beam strength for each of the radiation beams which will produce the radiation dosages within the prescribed limits at the selected points are automatically and electronically determined. Linear programming techniques are advantageously utilized to optimize for radiation uniformity and overall low dosage. The linear programming technique provides a solution to the set of simultaneous linear inequalities which are equal in number to the number of selected points within the contour and which have as variables the beam strengths necessary from each of the preselected radiation beams. The contribution of each of the radiation beams at each point is selected to be less than or greater than a predetermined desired dosage, and the set of inequalities describing such constraints are solved, preferably with the aid of a computer. The integral radiation dose is minimized as the objective function. If the original constraints provide no acceptable solution, the operator may relax the dosage limits at certain of the selected points and the new objective function becomes the minimization of the deviation of the dosages from the original limits at the relaxed points. If the resultant isodose pattern is acceptable, a hard copy may be obtained by use of a plotter. The operator may select other points and assign dosage limits based on the preceding isodose pattern.

BRIEF DESCRIPTION OF THE DRAWINGS

Various objects, features and attendant advantages of the present invention will be more fully appreciated as the same becomes better understood from the following detailed description of the present invention when taken in connection with the accompanying drawings, in which.

DETAILED DESCRIPTION OF A PREFERRED EMBODIMENT

The novel radiation treatment planning technique of the present invention permits the operator/therapist to impose limits on dosages at various selected points in the patient's cross section. Typically, lower limits of radiation dosage are imposed at the site of the tumor, while upper limits are imposed in the vicinity of the surrounding area or near other vulnerable tissue. These preselected dosage limits form a set of contraints on field strengths for each of a plurality of externally applied radiation beams. These constraints may be conveniently formulated in a linear programming model which may be solved, for example, by a digital computer. In other words, the computer will attempt to determine an optimal set of field strengths for a given number of externally applied radiation beams, which, when combined with the given patient's contour, will create dosages that lie within the imposed limits. It may occur that during the first trial, the desired limits may not be attainable, or may not produce the desired effect, whereupon an iterative process of adjusting the limits may be initiated, as will be described in more detail hereinafter.

Figure 1:
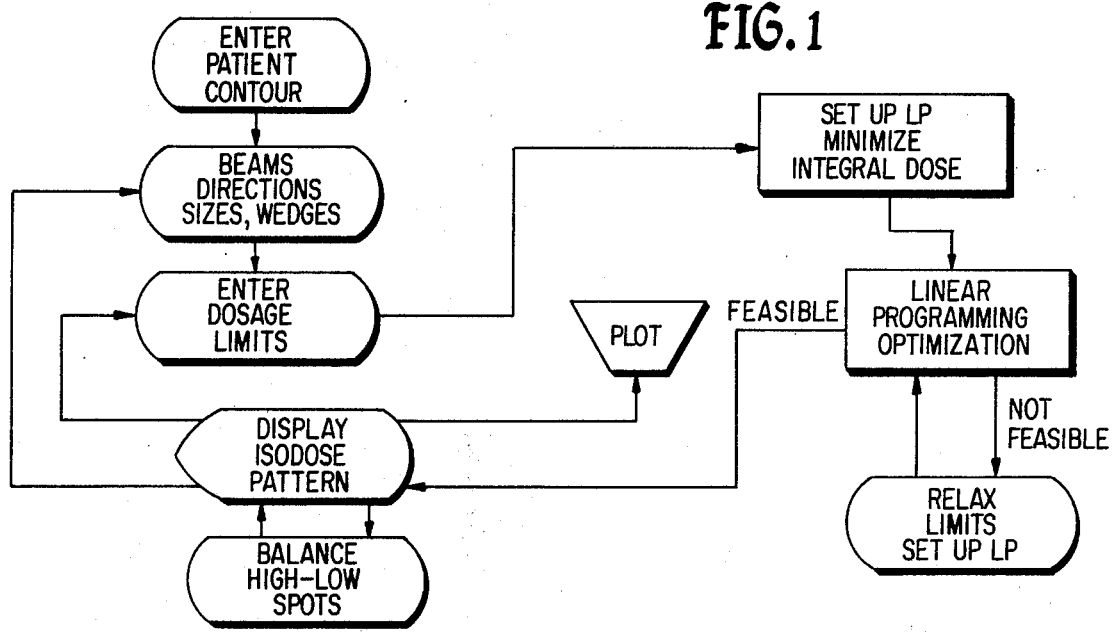
FIG. 1 illustrates a flow chart helpful in understanding the technique embodied by the present invention.
Figure 2:
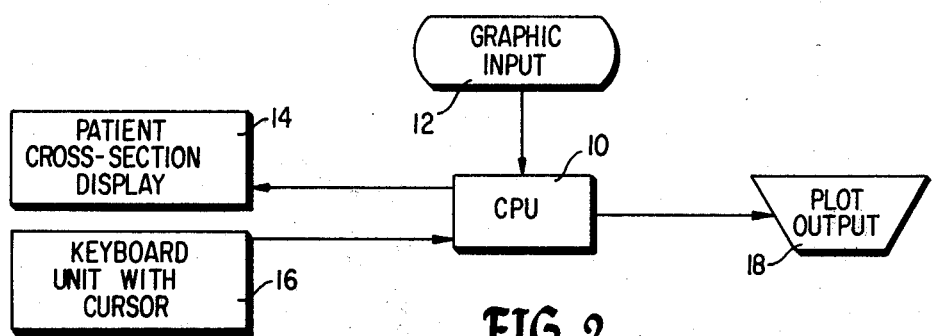
FIG. 2 is a block diagram showing apparatus which may be utilized in carrying out the technique of the present invention.

FIGS. 1 and 2 respectively illustrate a flow chart setting forth the interactive steps which comprise the technique of the present invention and a block diagram illustrating one possible component interconnection for achieving the method of the present invention. The structure depicted in FIG. 2 comprises a central processing unit 10 which receives as inputs signals representing a graphical display from graphic input 12 and signals from a keyboard unit with a light cursor 16. Central processing unit 10 provides an output by means of either an oscilloscopic display 14 or a hard-copy plotter 18. All of the foregoing components are well known in the art, and therefore need not be described herein in detail. Suffice it to say that components similar to those described in the abovementioned Holmes article may be utilizied to carry out the present technique with minor modifications, as will be apparent to and within the obvious abilities of a person skilled in the art.

The intial step in the present technique is for the operator/therapist to enter the patient's cross section into the computer by means of graphic input 12, which may comprise a position transducer. In addition to tracing the external contour of the patient and the tumor, the outlines of other relevant or sensitive areas are entered. The operator then selects the desired number of radiation beams, as well as their directions, sizes, and wedges. The operator may select more than one beam at a single direction, each having different sizes and/or wedges. It should be noted that in contrast to the prior art treatment planning techniques, the beam strength of each of the radiation beams is not prespecified.

The next step in the procedure is for the operator to select desired dosage limits at various selected points on the patient's cross section. The patient's cross section may be displayed on display unit 14 of FIG. 2, and the selection of the various points at which the dosage constraints are imposed may be done by means of light pen (cursor) in conjunction with keyboard unit 16. Alternatively, the dosage limits may be entered along with the patient's contour by graphic input 12.

Thereafter, central processing unit 10 will attempt to define those field strengths which satisfy the beam constraints and dosage limits. This can conveniently be achieved with the aid of a mathematical technique known as linear programming. An extensive discussion of linear programming techniques are omitted for the sake of brevity; however, reference is made to the mathematical summary appearing at pages 3 through 11 of "Linear Programming and Associated Techniques" by Riley and Gass, Johns Hopkins' Press, 1958 such disclosure being incorporated herein by reference thereto. One skilled in the art will appreciate that a set of simultaneous linear inequalities corresponding in number to the number of points selected in the cross section may be defined along with a variable created for each field. As the objective function for the linear programming analysis, the integral dose, i.e. the summation of the entire dosage over the whole cross section, is minimized. If the computer is able to provide a solution to the set of field strengths for each of the selected beams operating within the dosage limits, the solution may be displayed on display unit 14 as an isodose pattern superimposed on the patient's cross sectional contour. Further, the field strengths and directions of the non-zero strength fields may be displayed. Preselected beams are considered eliminated from a solution by an assignment of zero field strength. The operator/therapist may accept this solution or may try other beam directions or sizes or wedges. He may alternatively reset certain dosage limits at certain points in an attempt to achieve a more favorable solution. Further, if the solution merely requires a simple balancing of high and low dosage spots, the operator may indicate the spots to be balanced by means of the light cursor and designate them as high, low or hold constant. The computer may then calculate the most effective balance and display the result.

On the first attempt at arriving at a solution via linear programming, it may be found that a feasible solution does not exist since the constraints imposed by the operator may be too stringent. In such a case, the operator may indicate dosage limits at certain points by means of the light cursor which are thereby relaxed. Normally, the operator will relax upper limits, since lower limits are considered a necessary dose at the tumor site. The relaxed limits are no longer considered inviolate; but the computer will then attempt to obtain a linear programming solution which deviates as little as possible at these relaxed limits while satisfying all other limits. In other words, the new objective function for the linear programming model then becomes the minimization of the deviation from the previously selected limits at the relaxed points. This step will not be repeated indefinitely, inasmuch as a solution will always eventually be found, for example, when all of the upper limits are relaxed.

Figure 3:
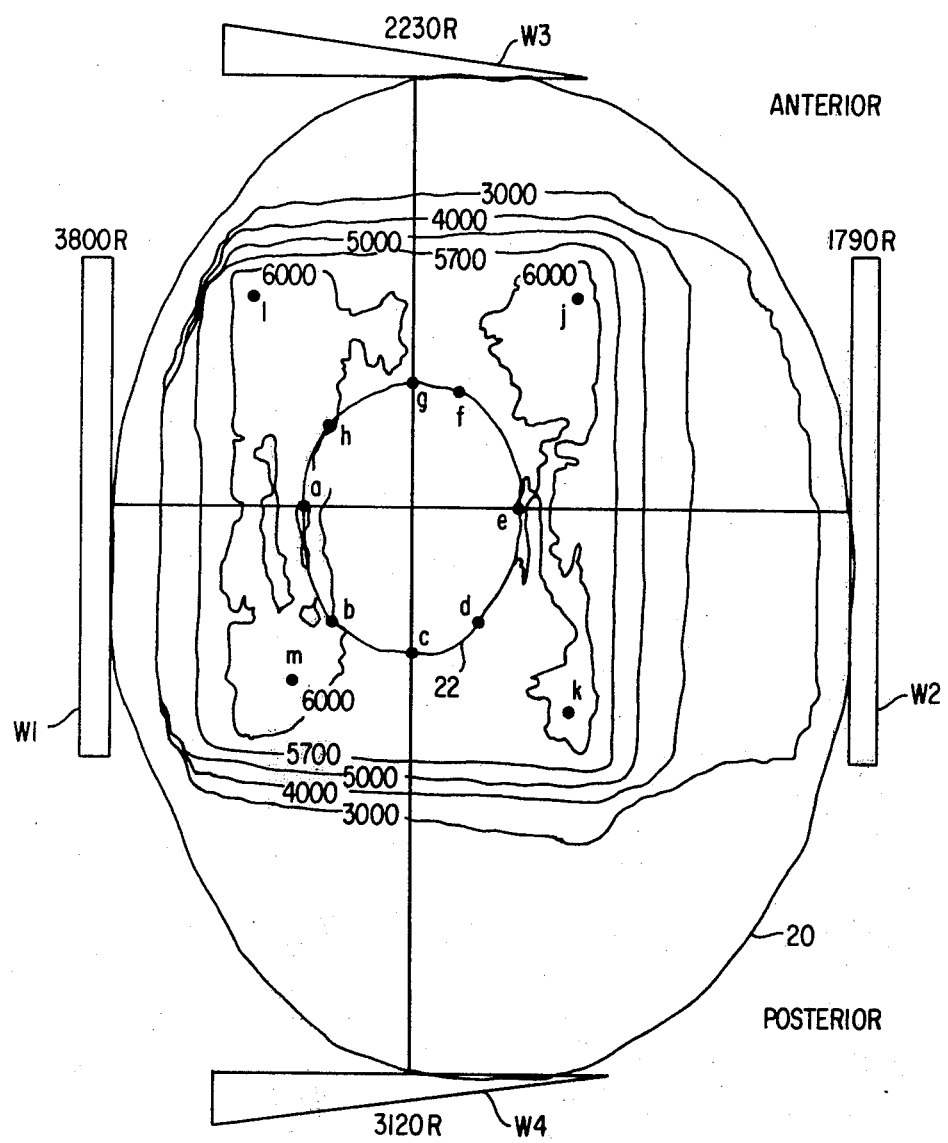
FIG. 3 illustrates the output of a plotter in a sample treatment plan helpful in understanding the principles of the present invention.

Referring now to FIG. 3, there is shown the final selected output from a plotter for an actual four-beam treatment plan in which the beam strengths, sizes and directions were preselected, as in the prior art techniques for the given patient's cross-sectional contour. The leftmost beam W1 was selected to have a field strength of 3800 rad. The rightmost beam W2 has a strength of 1790 rad, the anterior wedge beam W3 has a strength of 2230 rad, and the posterior wedge beam W4 has the assigned strength of 3120 rad. The outline designated by the reference numeral 20 indicates the cross-section of the patient's head with the outline of a brain tumor 22 appearing somewhat off center. The left and right fields W1 and W2 were each selected as 10 cm by 10 cm beams, while the anterior and posterior wedge fields W3 and W4 were each 8 cm by 10 cm. The isodose pattern resulting from the four beams W1 through W4 is shown within head contour 20 and are indicated by their relative resultant dosages. The isodose pattern depicted in FIG. 3 was obtained by means of the prior art Programmed Console as described earlier with the beam fields W1 through W4 being preselected as shown.

The isodose pattern depicted in FIG. 3 was utilized as a starting point to verify the accuracy of the technique of the present invention. In applying the technique of the present invention to the desired treatment plan illustrated in FIG. 3, it is seen that at least 6,000 rad is required at the center of tumor 22 while the dose should be limited to at most 6,000 rad at eight points, labeled $a$ through $h$, around the border of the tumor 22. Linear programming techniques would result in a set of nine simultaneous linear inequalities, each of which has the general form:

$$\alpha_{a1}W_1 + \alpha_{a2}W_2 + ... + \alpha_{an}W_n \gtreqless R_a$$

wherein $n$ is the number of desired radiation beams, $R_a$ represents a desired dosage limit at preselected point a within the contour, $\alpha_{an}$ represents the attenuation constant for beam $W_n$ to point a, and $W_n$ represents the desired beam strength.

Each radiation beam has a characteristic pattern of attenuation within the tissue, and the attenuation constants $\alpha_{an}$ are functions of beam position, size, and wedge angle, as well as the distances from the point of measurement, and are readily available from standard tables. For the points a through $h$, as well as for the center of the tumor, the set of inequalities shown below would be derived by the computer in accordance with the preselected beams' positions, sizes and wedge angles in coordination with the patient's contour:

| | | | | | | | | | |
|---|---|---|---|---|---|---|---|---|---|
| a: | .85W1 | + | .53W2 | + | .37W3 | + | .32W4 | ≤ | 6000 |
| b: | .82W1 | + | .54W2 | + | .33W3 | + | .38W4 | ≤ | 6000 |
| c: | .72W1 | + | .61W2 | + | .35W3 | + | .44W4 | ≤ | 6000 |
| d: | .67W1 | + | .67W2 | + | .40W3 | + | .44W4 | ≤ | 6000 |
| e: | .65W1 | + | .72W2 | + | .47W3 | + | .39W4 | ≤ | 6000 |
| f: | .69W1 | + | .66W2 | + | .53W3 | + | .32W4 | ≤ | 6000 |
| g: | .75W1 | + | .60W2 | + | .50W3 | + | .30W4 | ≤ | 6000 |
| h: | .83W1 | + | .55W2 | + | .43W3 | + | .29W4 | ≤ | 6000 |
| Center: | .75W1 | + | .62W2 | + | .42W3 | + | .36W4 | ≥ | 6000 |

The computer, programmed in a well-known manner, would attempt to solve the linear programming problem as constrained by the foregoing inequalities and utilizing as an objective function the minimization of the integral dose. The integral dose is expressed as the linear combination of the field strengths and may be conveniently estimated, as was done for the present example, by adding the contribution from each of the fields W1 through W4 in accordance with the formulas given by Johns and Cunningham in *The Physics of Radiology*, 3rd ed., 1969, p. 414 such formulas being incorporated herein by reference thereto. The computer, of course, has the capability of summing the individual contributions over a uniform grid of points, thereby permitting a more accurate determination of the integral dose.

Figure 4:
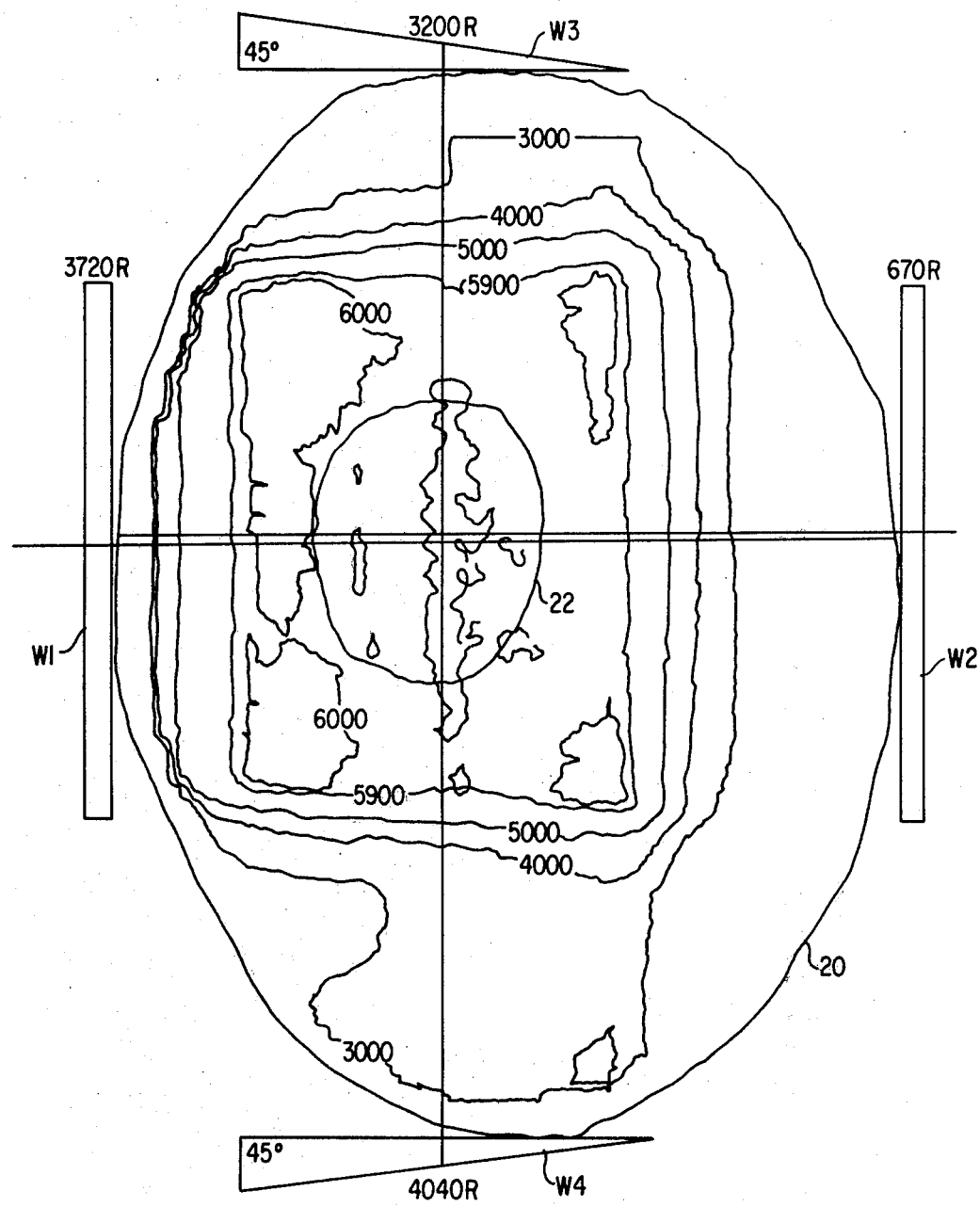
FIG. 4 illustrates an isodose pattern obtained by applying the method of the present invention.

The result of applying the technique of the present invention with the above constants is illustrated in FIG. 4, which compares favorably with the original plan shown in FIG. 3. The minimum integral dose was $8.8 \times 10^6$ gm rad. Although there appears to be large differences in the field strengths of the beams W1 through W4 from the original plan shown in FIG. 3, notice that the tumor dose distribution is not dissimilar. The integral dose of the original plan shown in FIG. 3, estimated by the same formula utilized above, was $8.9 \times 10^6$ gm rad, roughly 1% greater than the minimum for the set of beams depicted in FIG. 4.

The following illustrates a manner of utilizing the technique of the present invention in a more advantageous and powerful way. As starting points, still with reference to the original plan of FIG. 3, the skilled operator may select both wedge fields and regular fields at each of the four directions. That is, at the anterior and posterior directions 8 cm × 10 cm rectangular fields may be selected in addition to the 8 cm × 10 cm wedge fields used previously. Further, at the left and right sides, in addition to the 10 cm × 10 cm fields used previously, one may select 10 cm × 10 cm wedge fields and, just to cover all possibilities, 8 cm × 10 cm wedge fields. Thus, a total of 10 fields in the four directions have been selected. As the next step, dosage limits are assigned to certain points in the cross-section in order to get a uniform dose distribution. Referring again to the original plan seen in FIG. 3, it is seen that one would wish to apply at least 6000 rad around tumor 22; thus, lower limits of 6000 rad at each of the eight points $a$ through $h$ are selected. Simultaneously, an upper limit of 6000 rad at each of the same eight points are also selected. Accordingly, any solution to the foregoing constraints would have a dosage of exactly 6000 rad at all eight points $a$ through $h$. In addition to points $a$ through $h$, four points labeled $j, k, l$ and $m$ are selected whose contributions from two or more fields would be superimposed, and the dosage is selected to be limited at each of these four points to 6000 rad as an upper limit.

The computer would then set up a linear programming problem containing $(2 \times 8 + 4) = 20$ inequalities over 10 variables. That is, one inequality is created for each point constraint selected and a variable is created for each field selected. The linear programming problem, again minimizing the integral dose, fails to be solved. That is, there is no dosage distribution, even including all 10 preselected fields, which satisfy the given constraints.

In accordance with the technique of the present invention, some of the dosage limits may now be relaxed. For the sake of simplicity with respect to the instant example, all of the upper limits at all 12 points $a$ through $m$ were relaxed. A solution should be forthcoming which has the following characteristics. The dosage at the eight points $a$ through $h$ around the periphery of tumor 22 should be at least 6000 rad. Further, the largest amount by which the final dosage will exceed 6000 rad at the 12 points $a$ through $m$ will be as small as possible. The foregoing provides the desired optimization for uniformity. The solution yielded a maximum dosage of 6025 rad which occured at points $b, e, f$ and $h$. The eight points around the tumor $a$ through $h$ would thus have a dosage range from 6000 to 6025 rad, a variation of less than 0.5 percent. The field strengths for each of the ten beams required to produce such a dosage distribution obtained by the linear programming solution are shown in Table 1 below:

TABLE 1

| Beam | Field Strength |
|---|---|
| LEFT | |
| 10 cm. × 10 cm. | 3316 R (W1) |
| 10 cm. × 10 cm. wedge | 0 |
| 8 cm. × 10 cm. wedge | 406 R |
| RIGHT | |
| 10 cm. × 10 cm. | 329 R |
| 10 cm. × 10 cm. wedge | 0 |
| 8 cm. × 10 cm. wedge | 1333 R (W2) |
| ANTERIOR | |
| 8 cm. × 10 cm. wedge | 2985 R (W3) |
| 8 cm. × 10 cm. | 424 R |
| POSTERIOR | |
| 8 cm. × 10 cm. wedge | 2852 R (W4) |
| 8 cm. × 10 cm. | 39 R |

It may be observed from Table 1 that four of the fields (labeled W1, W2, W3, and W4) out of the ten completely dominate the others. The four large fields are the left 10 cm. × 10 cm. field, and the right, anterior and posterior 8 cm × 10 cm. wedge fields. It is apparent that these four dominant fields differ from the original four fields preselected in the plan shown in FIG. 3 in having a wedge to the right.

Figure 5:
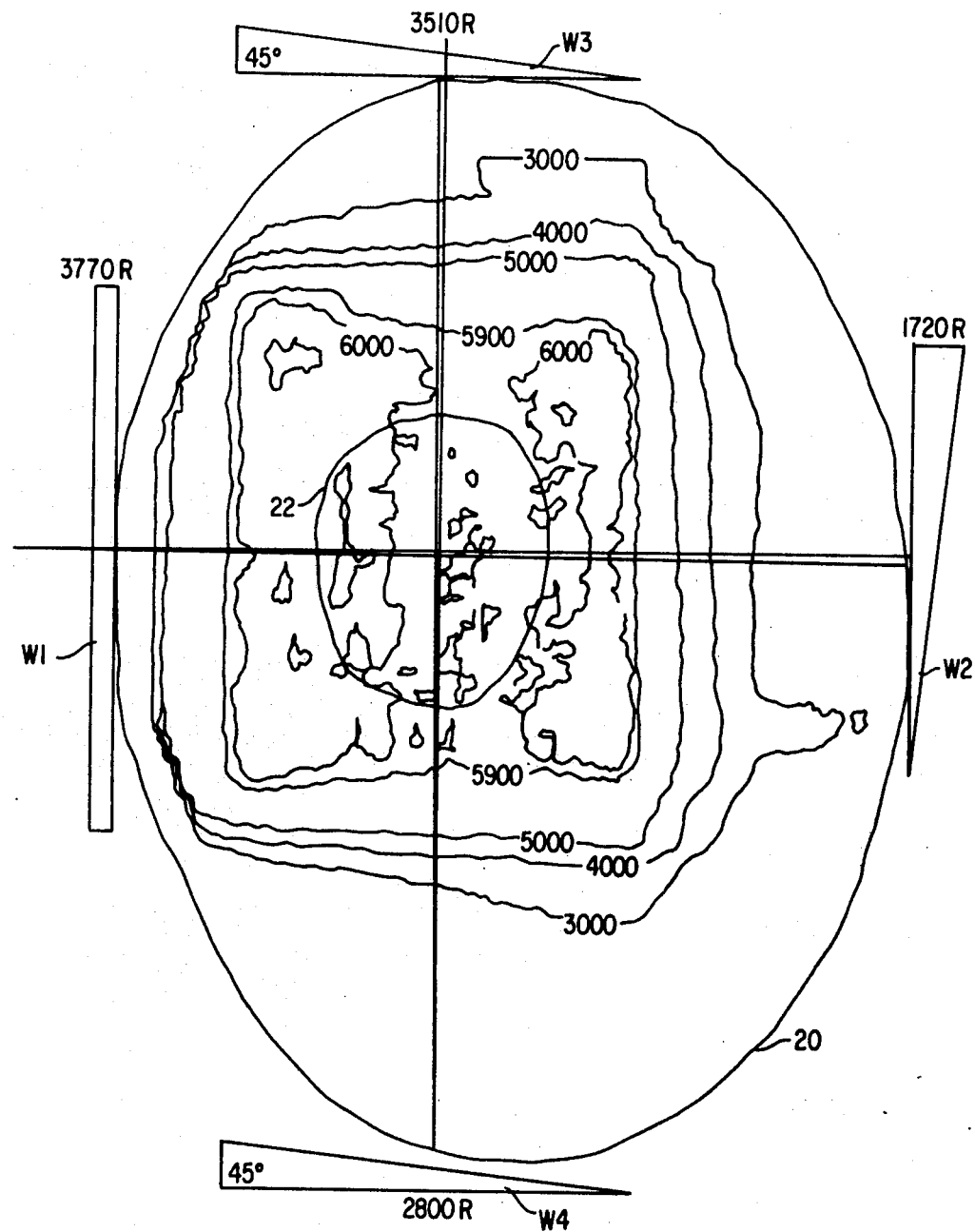
FIG. 5 illustrates an isodose pattern illustrative of an alternative treatment plan according to the technique of the present invention.

In accordance with the technique of the present invention, the planning procedure may now be iterated using the dominating four fields W1, W2, W3 and W4 as outlined above. Accordingly, the next solution will specify the strength necessary for just four beams instead of all ten. The dosage limits were maintained the same as when the ten beams were used. Once again, no feasible solution appeared, and the upper limits were relaxed. The resultant solution showing the isodose pattern and the field strengths for each of the four beams W1 through W4 is shown in FIG. 5. Note that the solution has a maximum of 6038 rad at any of the 12 points. It should be further noted that the solution resulting from the iterative procedure provides a quite uniform distribution, and further that the larger doses are applied at the left and front of the cross section where the tumor is closer. This has the effect of lessening the non-tumor dose versus tumor dose ratio. The integral dose estimates to $8.6 \times 10^6$ gm rad, now a significant improvement over the original plan. Accordingly, It is seen that, in the instant example, a wedge beam can be quite useful at the right of the contour, as well as at the anterior and posterior positions. This was naturally overlooked by the originators of the plan shown in FIG. 3, but provides a significant illustration of how the technique of the present invention provides, automatically, a previously unconsidered improvement over the original plan.

Although linear programming has been seen to be a powerful optimization tool, one must be extremely careful when applying it to treatment planning. The reason is that one aspect of linear programming is fundamentally opposed to one of the goals in treatment planning. That is, linear programming solutions are always given in terms of so-called extreme points, and this will generally violate the characteristic of uniformity desirable in a treatment plan.

Figure 6:
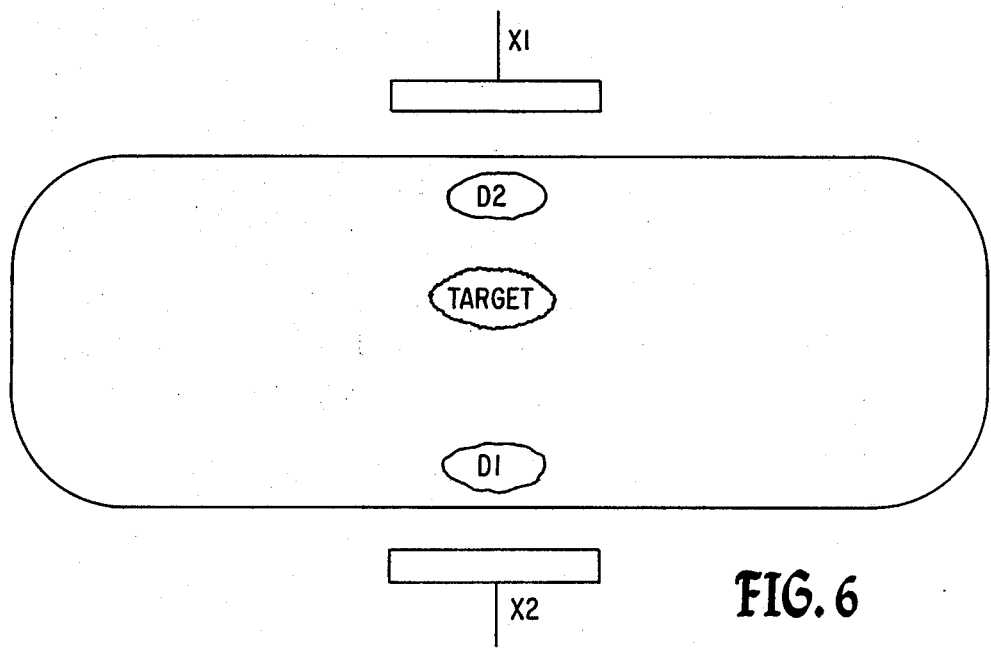
FIG. 6 is a schematic diagram of a radiation therapy unit useful in connection with understanding the linear programming principles according to the present invention.

Referring now to FIG. 6 as an example, suppose, in an oversimplified case, one has two fields, X1 and X2, with the requirement that 0.5X1 + 0.4X2 = 1, and suppose further, that there exist two sensitive areas requiring dosages of D1 and D2, where D1 = 0.2X1 + 0.8X2 and D2 = 0.8X1 + 0.2X2. Then, if it is desired to minimize D1 + D2, which one can do conveniently by linear programming, the result will be X1=2 and X2=0. Thus, D1=4 and D2=1.6, which would clearly be much too lopsided for a satisfactory treatment plan.

Notice that it is not merely a poor choice of direction for the beams but misuse of linear programming which can cause large nonuniformity in the resulting plan.

One way to avoid much of the above difficulty is to minimize not D1 + D2, but the maximum of D1 and D2. This leads to piecewise linear programming and can yield to the methods of Hodes, L.: "Solving Problems by Formula Manipulation in Logic and Linear Inequalities", *Artificial Intelligence Journal*, Vol. 3, (1972) pp, 165–174 such disclosure being incorporated herein be reference thereto. In this example, one would get D1=D2=1.11. The same effect is produced here by introducing a new variable Z together with the inequalities D1 ≤ Z and D2 ≤ Z, and then minimize Z by linear programming. In other words, linear programming is forced to optimize for uniformity, as well as low dosage to certain points.

It is noted that there is a tendency to set limits which are too stringent to be satisfied by any combination of field strengths; ie., to try for a better plan that can be realized. Now it is seen that there is also the opposite danger of specifying dosage limits in such a way that too much leeway is allowed for the linear programming solution. In that case one can observe the aforementioned lopsidedness. This can be corrected interactively by choosing appropriate high and/or low spots and setting further dosage limits thereon.

It is seen by virtue of the foregoing examples that linear programming techniques aid in providing a good radiation therapy treatment plan if the dosage limits are well specified. Further, the speed and capacity of linear programming techniques are more than adequate. If the small, on-site computer has poor arithmetic capabilities, one can transmit the linear programming problems to a standard time-sharing system very quickly, since large amounts of data do not have to be transmitted. Accordingly, it is seen that the operator/therapist may specify five, six or a dozen beams by their sizes, wedges, and directions. Further, 10, 15 or 20 dosage limits may be specified at various critical points on the patient's cross-section. The operator will then quickly get back the response, i.e. the field strengths for the various beams selected; the isodose pattern for the solution being displayed concurrently.

The present technique is therefore seen to comprise a novel and unique method of radiation therapy treatment planning which eliminates much of the guesswork required of prior art techniques. By enabling the operator/therapist to prespecify the desired end result, rather than merely guess at the parameters that may or may not achieve that result, he is provided with a much more powerful tool in the overall planning process. Costly computer time and man-hours of labor are thereby conserved, and results may be achieved which would normally not be investigated nor expected by means of the prior art techniques.

Obviously, numerous modifications and variations of the present invention are possible in light of the above teachings. It is therefore to be understood that within the scope of the appended claims the invention may be practiced otherwise that as specifically described herein.

I claim:

1. An improved method of radiation therapy treatment planning enabling the production and display of a desirable radiation dosage distribution from a predetermined number and arrangement of simulated radiation sources, said method comprising the steps of:
   electronically plotting a simulation of the contour of the areas of interest of the patient desired to be treated;
   selecting a predetermined number of simulated sources of radiation of known beam sizes and wedges and electronically orienting and directing said simulated radiation sources about the patient contour;
   setting radiation dosage limits at a plurality of points within the patient contour;
   automatically determining the beam strength for each of the predetermined number of oriented sources of simulated radiation which will result in radiation dosages within the set limits at the points within the patient contour;
   manually intervening by readjusting certain of the radiation dosage limits in the patient contour should the previous step fail to yield a beam strength dosage distribution resulting in radiation dosages within the initially set limits at the points within the patient contour;
   automatically redetermining the beam strength for each of the predetermined number of oriented sources of simulated radiation which will result in radiation dosages within the readjusted limits at the points within the patient contour;
   repeating the preceeding two steps until the radiation dosages fall within the readjusted limits; and
   displaying the resulting isodose pattern;
   whereafter radiation therapy to the areas of interest of the patient can be effected with the same oriented and predetermined number of actual radiation sources having the determined beam strengths.

2. The method of treatment planning according to claim 1, wherein said step of automatically determining the beam strength for each of said oriented simulated sources of radiation includes the step of electronically solving a set of simultaneous linear inequalities corresponding in number to the number of said points within said contour.

3. The method of treatment planning according to claim 2, wherein each of said linear inequalities is of the form:

$$\alpha_{a1}W_1 + \alpha_{a2}W_2 + \ldots + \alpha_{an}W_n \gtreqless R_a$$

wherein $n$ is the number of simulated sources of radiation, $R_a$ represents a set dosage limit at point a within said contour, $\alpha_{an}$ equals the attenuation constant from source n to point a, and $W_n$ equals the beam strength of source $n$.

4. The method of treatment planning according to claim 3, wherein said set of simultaneous inequalities are solved by means of linear programming techniques wherein the integral radiation dose is minimized as the objective function.

5. The method of treatment planning according to claim 4, wherein said step of automatically redetermining the beam strength for each of said simulated sources of radiation includes the step of electronically solving a set of simultaneous linear inequalities corresponding in number to the number of said points within said contour by means of linear programming techniques wherein the deviation of said radiation dosages from said limits is minimized as the objective function.

6. The method according to claim 1 wherein the step of displaying the resulting isodose pattern comprises electronically plotting the isodose pattern superimposed on said contour as a result of the determination of the beam strength for each of said simulated radiation beams.

* * * * *